United States Patent [19]

Nagata et al.

[11] Patent Number: 5,070,733

[45] Date of Patent: Dec. 10, 1991

[54] PHOTOACOUSTIC IMAGING METHOD

[75] Inventors: Yoshihiko Nagata, Tsukuba; Toshio Koda, Ushiku, both of Japan

[73] Assignee: Agency of Industrial Science & Technology, Ministry of International Trade & Industry, Tokyo, Japan

[21] Appl. No.: 409,313

[22] Filed: Sep. 19, 1989

[30] Foreign Application Priority Data

Sep. 21, 1988 [JP] Japan .................................. 63-236899

[51] Int. Cl.$^5$ ................................................ G01N 9/24
[52] U.S. Cl. ........................................ 73/602; 73/606; 73/643
[58] Field of Search ........................... 73/602, 606, 643

[56] References Cited

U.S. PATENT DOCUMENTS

| 4,255,971 | 3/1981 | Rosencwaig | 73/603 |
| 4,484,820 | 11/1984 | Rosencwaig | 374/6 |
| 4,513,384 | 4/1985 | Rosencwaig | 364/563 |
| 4,518,992 | 5/1985 | Kessler et al. | 73/606 |

Primary Examiner—Hezron E. Williams
Assistant Examiner—William Francos
Attorney, Agent, or Firm—Oblon, Spivak, McClelland, Maier & Neustadt

[57] ABSTRACT

A photoacoustic imaging method comprises the steps of using modulated light of two different modulation frequencies to illuminate an object to be observed, so that an image of only a region of a specified depth within the object is obtained based on the difference between two photoacoustic signals separately detected by an acoustic sensor.

2 Claims, 5 Drawing Sheets

PHOTOACOUSTIC IMAGING METHOD

BACKGROUND OF THE INVENTION

1. Field of the Invention

This invention relates to a photoacoustic imaging method for nondestructively obtaining planar images of an object cut at any desired depth beneath its surface.

2. Prior Art Statement

When an object is illuminated with modulated light, the light absorbed by the object is intermittently converted to heat, thus generating sound caused by the accompanying thermal strain.

A photoacoustic signal obtained by extracting this sound as a signal varies with respect to physical properties of the object including its absorptance of light, the speed of conduction of heat through the object and various other properties, so by using this photoacoustic effect, the interior of the object can be observed in a nondestructive manner.

Microscopes which exploit the photoacoustic effect in this manner, e.g. U.S. Pat. No. 4,255,971, have been disclosed, and are being employed in the nondestructive inspection of the interior of products which cannot be seen with visible light.

The resolution of these photoacoustic microscopes in the direction of the two-dimensional surface illuminated by modulated light is dependent on the spot diameter of the incident light. Resolution in the depth direction of the illuminated surface is dependent on the thermal diffusion length, or the distance over which heat travels through the object during one cycle of the modulated light. Therefore, increasing the modulation frequency decreases the thermal diffusion length, so as shown in FIG. 1(a), a photoacoustic signal is generated from a region 3a near the surface of an object 2 illuminated by modulated light 1, and thus this region can be observed, but a defect area 4 located deeper within the object and outside of the signal-generating region cannot be observed. On the other hand, if the modulation frequency is decreased, the thermal diffusion length increases so as shown in FIG. 1(b), a photoacoustic signal is generated from a wide region 3b which includes areas located both near the surface and deep under the surface, so the defect area 4 can be observed even if it is present deep within the object. However in this case, photoacoustic signals from areas which need not be observed (shallow areas near the surface of the object) become noise which is incorporated into the detected photoacoustic signal, greatly affecting it so that a clear image of the defect area 4 only cannot be obtained.

Therefore, in the present situation, an appropriate modulation frequency must be selected depending on the type of object to be observed.

The object of this invention is to supply a photoacoustic imaging method through which one is able to nondestructively obtain clear planar images at any desired depth from the surface of an object.

OBJECT AND SUMMARY OF THE INVENTION

In order to solve the above problem, when an object to be observed is illuminated with modulated light and a photoacoustic signal generated by thermal strain of said object is sensed by an acoustic sensor, amplified and converted to an image, the photoacoustic imaging method of the present invention comprises the steps of using modulated light of two different modulation frequencies to illuminate said object to be observed and obtaining an image based on any ratio of intensities or phase differences between two photoacoustic signals detected by said acoustic sensor.

As described above, different frequencies of modulated light with which the object is illuminated will give different thermal diffusion lengths within the object, so by finding the ratio of intensities or phase differences between the photoacoustic- signals from the two types of modulated light of different frequencies, an image of regions of differences between the two thermal diffusion lengths can be obtained. Thus by selecting two frequencies for the modulated light as needed, an image of a plane at the desired depth can be obtained without information from unwanted regions.

Other objects and other characteristics of the present invention will be made clear through the following detailed explanation with reference to the attached figures.

DETAILED DESCRIPTION OF THE PREFERRED EMBODIMENT

Figure 1A:
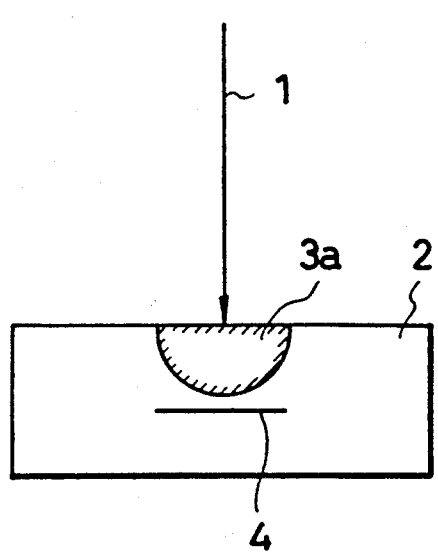
FIGS. 1(a) and 1(b) are diagrams used to explain the photoacoustic effect.
Figure 1B:
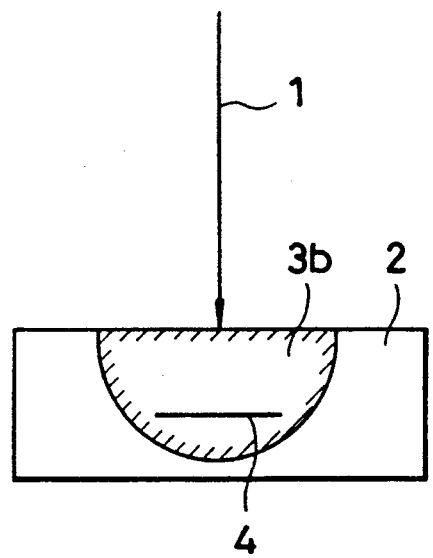
Figure 2:
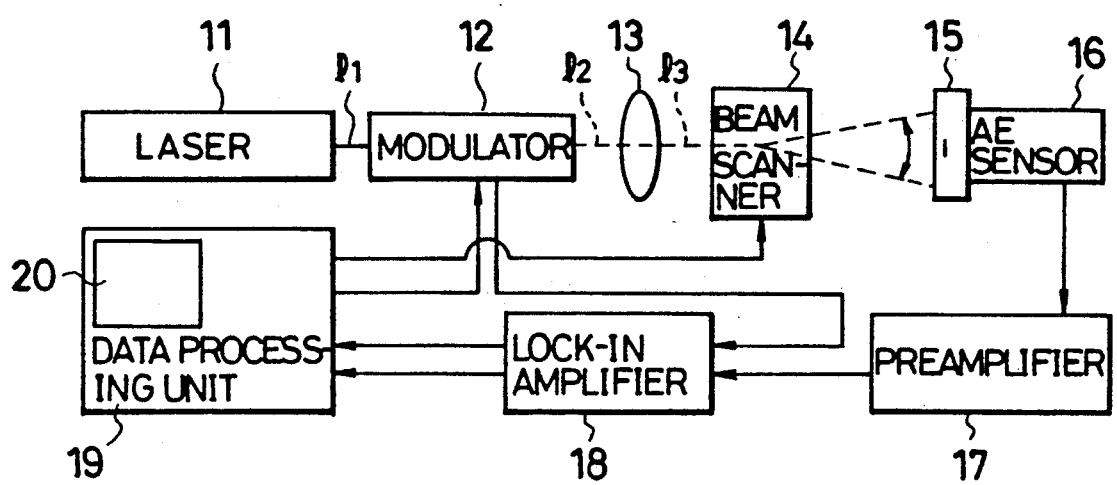
FIG. 2 is a block diagram illustrating a photoacoustic imaging device as a preferred embodiment of the method of this invention.

FIG. 2 is a block diagram illustrating a photoacoustic imaging device as a preferred embodiment of the method of this invention. Number 11 in the diagram is a He-Ne laser used as the light source. Arranged in line with the forward axis of the laser 11 are a modulator 12, optical system 13, and a two-axis beam scanner 14 in this order. The modulator 12 is provided with a facility allowing it to be set to any desired modulation frequency and the modulation frequency can be changed as needed.

An object to be observed 15 is arranged facing the two-axis beam scanner 14, and an acoustic sensor 16 is arranged on the rear surface of the object 15. By illuminating the object to be observed 15 with modulated light, a photoacoustic signal generated by the photoacoustic effect can be detected.

The weak photoacoustic signal detected by this acoustic sensor 16 is amplified by a preamplifier 17. A lock-in amplifier 18 synchronizes the amplified signal with a signal sent from the modulator 12 and the synchronized signal is processed by a data processing unit 19 and converted to an image on a screen 20.

In a photoacoustic imaging device of the above construction, the He-Ne laser 11 emits a laser beam $l_1$ toward modulator 12. The light source is not limited to being a laser; rather a light source which generates white light, for example, can also be used. The laser beam $l_1$ entering modulator 12 is modulated and exits as modulated light $l_2$ of a specified frequency depending on the depth of the region of the object to be observed. In other words, the thermal diffusion length $\mu$(m) and the light frequency f are related as follows, $$\mu = \left(\frac{\kappa}{\pi f \rho c}\right)^{\frac{1}{2}}$$

so if certain physical properties of the sample object are known, the frequency which generates the desired thermal diffusion length can be calculated from the above equation, where $\kappa$ is the thermal conductivity of the object, $\rho$ is the density of the object and c is the specific heat of the object. For example, if an image of a plane approximately 500 $\mu$m beneath the surface of a sample is to be obtained, the laser beam $l_1$ entering modulator 12 is first modulated so that it exits as modulated light $l_2$ of a frequency such that the thermal diffusion length becomes 600 $\mu$m.

This modulated light $l_2$ is focused by an optical system 13 of lenses or the like into a beam of parallel light of a desired diameter and sent to a beam scanner 14. Reducing the diameter of the beam of modulated light gives a higher resolution but also increases the amount of time required for scanning which is the next step, so the diameter should be appropriately selected by taking resolution and scanning time into consideration.

The beam scanner 14 illuminates the specified region on the object to be observed 15 with a series of consecutive scans of the beam of modulated light focused to the specified diameter $l_3$. When the object to be observed 15 is illuminated by scanning in this manner, sound obtained by means of the photoacoustic effect, or more specifically, sound generated by thermal strain which accompanies the conversion to heat of light intermittently absorbed by the object, is sequentially detected by an acoustic sensor 16 arranged behind the object to be observed 15.

The frequency of the modulator is set so that the thermal diffusion length becomes 600 $\mu$m, so the photoacoustic signal thus detected contains information for the region from the surface down to 600 $\mu$m below the surface.

The photoacoustic signal detected by the acoustic sensor 16 is amplified by the preamplifier 17 and sent to the lock-in amplifier 18. The lock-in amplifier 18 uses a frequency-modulated signal sent from the modulator 12 as a reference signal to remove the frequency-modulated component of the input photoacoustic signal and analyzes the remaining signal into its amplitude and phase components, which are sent to the data processing unit 19 as intensity (amplitude) and phase signals, and stored sequentially.

Once the scanning of the specified region of the object 15 is complete and the intensity signal and phase signal are stored, the modulator 12 is then manipulated to change the frequency of the modulated light to a frequency which will give a thermal diffusion length of, for example, 400 $\mu$m, and then this light is used to illuminate the specified region on the object to be observed 15 by scanning with the two-axis beam scanner 14 as described above.

The photoacoustic signal generated in the object from a region which depends on the thermal diffusion length and detected by this acoustic sensor 16 is amplified by a preamplifier 17. A lock-in amplifier 18 synchronizes the amplified signal with a modulated signal sent from the modulator 12 and sends an intensity signal and a phase signal to the data processing unit 19. These intensity and phase signals contain information for the region from the surface of the object down to 400 $\mu$m below the surface.

The data processing unit 19 calculates the difference between the previously stored intensity or phase signal containing information for the region from the object surface down to 600 $\mu$m with the newly obtained intensity or phase signal containing information for the region from the surface down to 400 $\mu$m. An image is created by finding the ratio of intensities when intensity signals are used, or by finding phase differences when phase signals are used. This results in an image of a region containing the desired depth of 500 $\mu$m between 400 $\mu$m and 600 $\mu$m below the surface of the object being displayed on the screen 20.

Figure 3A:
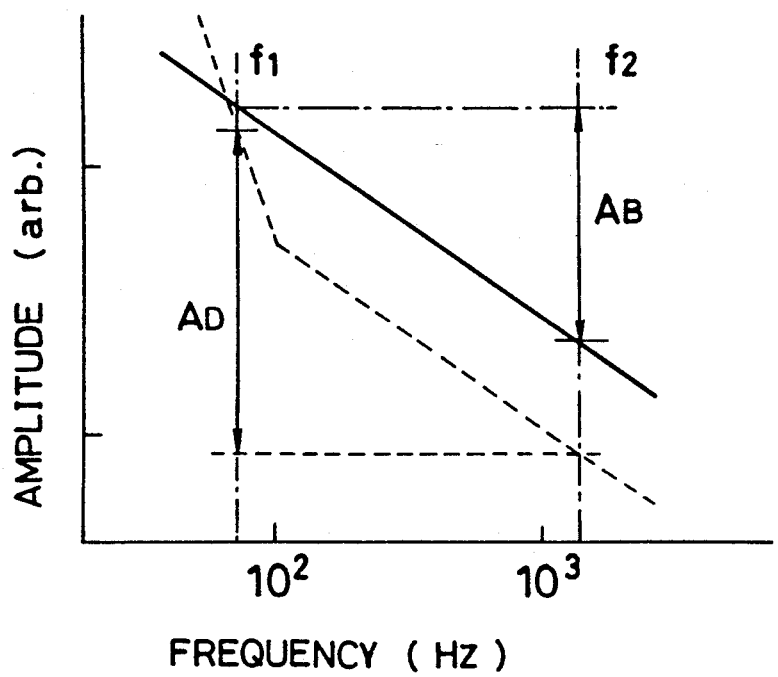
FIG. 3(a) is a graph of the intensity (amplitude) signal as a function of frequency.

Here follows an explanation of the method of using the data processing unit 19 to obtain an image based on the ratio of intensities between two signals of different frequencies. The solid line in FIG. 3(a) represents amplitude as a function of frequency at a defect-free location within the object. The dotted line in the figure represents amplitude as a function of frequency at a location which contains a defect. (The scale of the graph is logarithmic.) If the ratio of intensity of two intensity (amplitude) signals of frequencies $f_1$ and $f_2$ is always $A_6$, this means that no defects are present in the region between the thermal diffusion lengths of the two signals. If however the intensity signal of frequency $f_2$ is a low value which crosses the dotted line and the ratio of intensity becomes $A_D$, this means that there is a defect present in the region between the thermal diffusion lengths of the two signals. Therefore, the data processing unit 19 will sequentially find the ratio of intensity between two intensity signals of different frequencies at the same point in the region to be observed; if no defects are present this value will be $A_B$, and if defects are present this value will be a value other than $A_B$, namely $A_D$, so if a defect is present in the plane of a desired depth, it will be clearly displayed in the image.

Figure 3B:
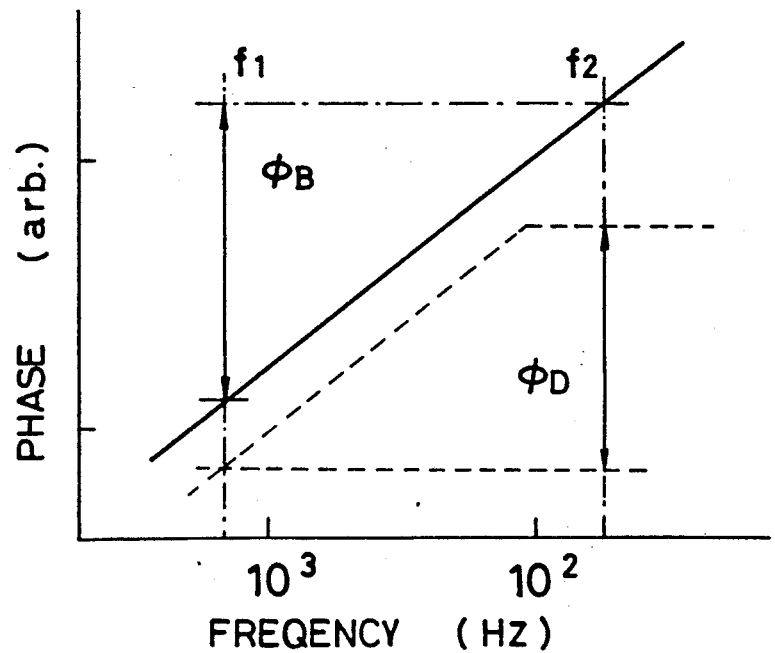
FIG. 3(b) is a graph of the phase signal as a function of frequency.

Here follows an explanation of the method of obtaining an image from phase differences between two signals of different frequencies. The solid line in FIG. 3(b) represents phase as a function of frequency at a location within the object which is free from defects. The dotted line in the figure represents phase as a function of frequency at a location which contains a defect. The difference between two phase signals of frequencies $f_1$ and $f_2$ is $\phi_B$ if there are no defects present at the desired depth in the location being observed, but if a defect is present this difference will become $\phi_D$. Thus as described above, by finding the difference between two intensity signals of different frequencies at the same point in the region to be observed and converting it to an image, any defects which may be present in the plane of a desired depth will be clearly displayed in the image.

As described above, by this invention, information from a plane at a desired depth may be obtained from either a ratio of intensities or phase difference between two signals of different frequencies, so the decision of which to use when carrying out imaging should be made when needed by taking the imaging conditions into consideration.

The present invention came about from the observation, as in the above, that changing the frequency of modulated light with which an object is illuminated will change the region (depth from the surface) from which a photoacoustic signal is generated, so by appropriately selecting two frequencies of modulated light with which the object is illuminated, photoacoustic signals from unwanted regions can be removed to nondestructively display an image of a region at any desired depth from the surface of the object.

Figure 4A:
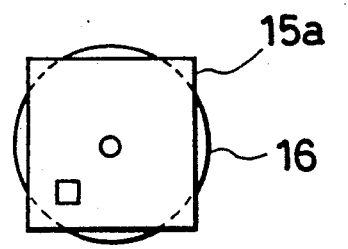
FIGS. 4(a) and 4(b) are diagrams used to explain samples used in experiments on this invention.

Two samples were prepared: sample 15a shown in FIG. 4(a), which is a copper plate measuring 15 mm on one side and 1 mm thick, and sample 15b made by using a press to imbed a copper plate of dimensions $8 \times 7 \times 0.5$ mm into the center of a copper plate of the same dimensions as sample 15a. A piezoelectric AE sensor (Fuji Ceramic, Japan, AE705S) was arranged as an acoustic sensor 16 behind each of the two samples 15a and 15b. A 0.1 mm diameter beam from a 30 mW laser was used to illuminate sample 15a at its center (the ○ symbol) and an area on its edge (the □ symbol) and sample 15b at its center (the symbol). The intensity signal and phase signal as a function of frequency were observed by measuring the photoacoustic signal at these locations with the acoustic sensor 16 while the frequency of the beam was varied between 10 and $10^4$ Hz. The thermal diffusivity of the sample copper plate at 20° C. is 117 mm$^2$/sec.

Figure 5A:
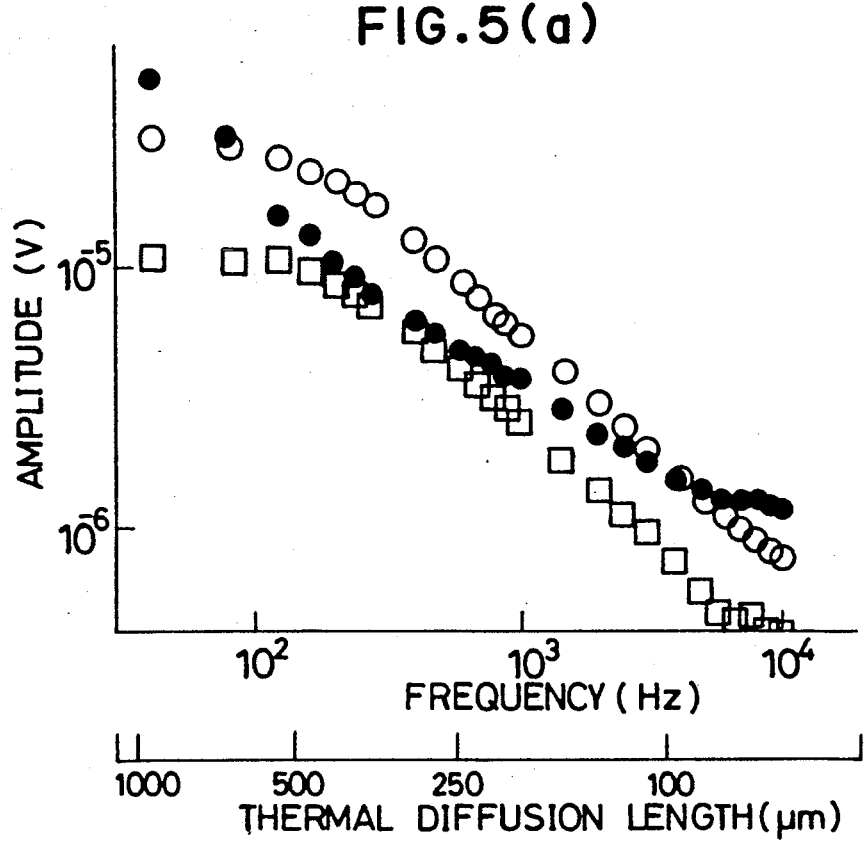
FIG. 5(a) is a graph of the intensity (amplitude) signal as a function of frequency when the samples of FIGS. 4(a) and 4(b) are illuminated with modulated light.
Figure 5B:
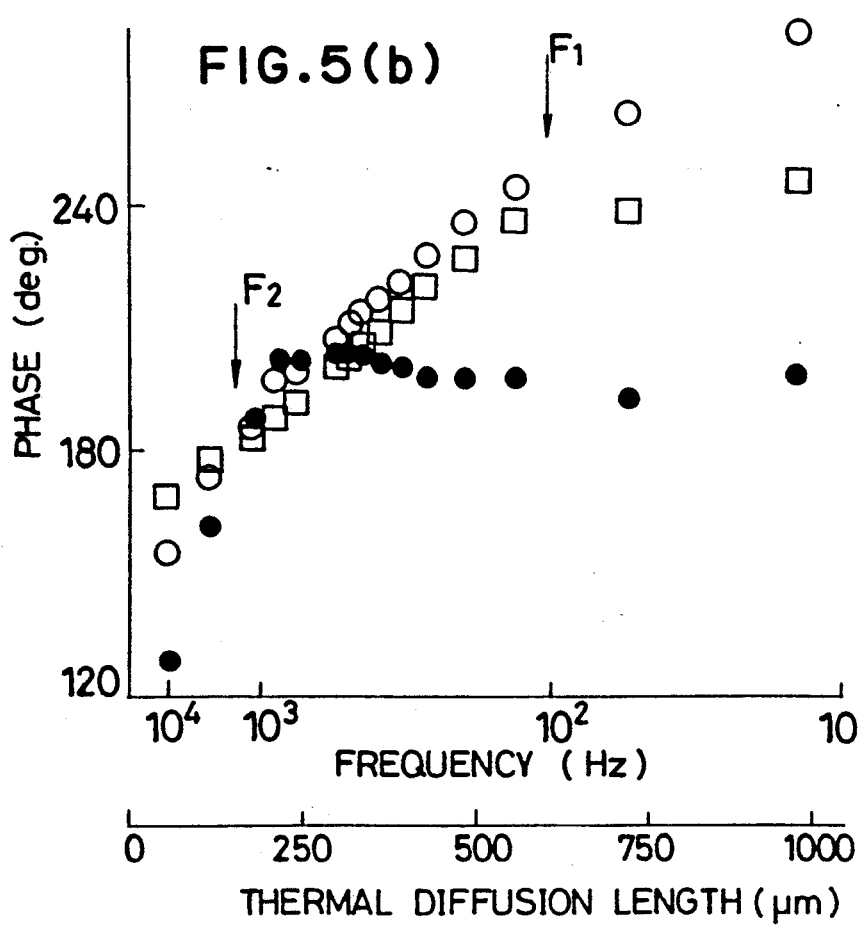
FIG. 5(b) is a graph of the phase signal as a function of frequency when the samples of FIGS. 4(a) and 4(b) are illuminated with modulated light.

FIGS. 5(a) and 5(b) illustrate the intensity signal as a function of frequency obtained in the experiment, and the phase signal as a function of frequency, respectively. In both cases of the sample 15a being illuminated in its center (the ○ symbol) and at an area on its edge (the □ symbol), the amplitude varied almost linearly with frequency in the range from 100 Hz to 3 KHz, and it was found that selecting any two frequencies and finding their ratio of intensities gives a constant value over this frequency range. Furthermore, upon calculating the phase difference, this difference was found to be constant. Thus in the sample with no defect, when the frequency of the modulated light is changed, while the intensity and phase obtained in the center and in the periphery of the sample are slightly different due to differences in the sensitivity of the sensor in its center and periphery, they vary almost linearly with frequency, indicating that the data is independent of whether the position of illumination is in the center or the periphery.

Figure 4B:
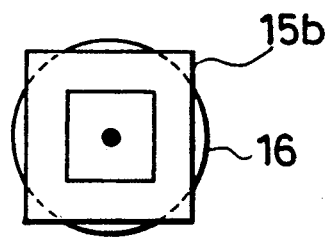

When illuminating the center of defect-containing sample 15b of FIG. 4(b), the values represented by the symbols in both FIGS. 5(a) and 5(b) do not parallel the values of the sample with no defect. This is particularly apparent in the phase graph in which the phase essentially ceases to change once the frequency becomes lower than 1 kHz. This is because the signal obtained by the sensor was found to be affected by the defect. Note that at high frequencies, the thermal diffusion length is so short as to be unaffected by the defect, so the values should be coincident with the ○ symbols, but the generated photoacoustic signal travels through the defect section before it is received by the sensor 16 so the defect section becomes noise which prevents the values from coinciding with the ○ symbols.

Figure 6A:
FIG. 6(a) is a photograph of an image based on a phase signal obtained when the sample of FIG. 4(b) is illuminated with modulated light of a frequency of 109 Hz.
Figure 6B:
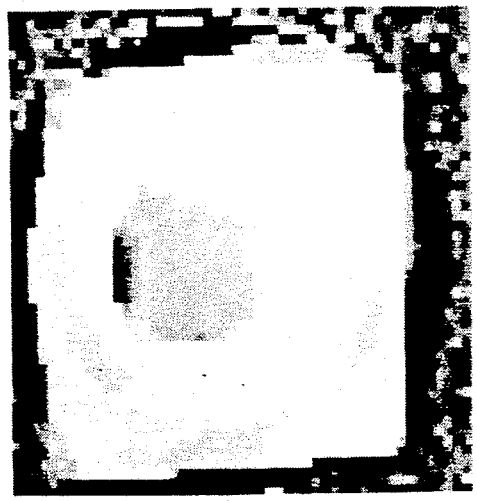
FIG. 6(b) is a photograph of an image based on a phase signal obtained when the same sample is illuminated with modulated light of a frequency of 2 KHz.

FIG. 6(a) is a photograph of an image obtained by processing the phase signal of a photoacoustic signal obtained by using modulated light of a frequency of 2 kHz (arrow $F_1$ on FIG. 5(b) to illuminate and scan the sample of FIG. 4(b). Since the frequency is high, the thermal diffusion length does not reach the defect so the defect section does not appear in the image. FIG. 6(b) is a photograph of an image obtained by processing the phase signal of a photoacoustic signal obtained by using modulated light of a frequency of 109 Hz (arrow $F_2$ on FIG. 5(b) to illuminate and scan the same sample. Since the frequency is low, the thermal diffusion length does reach the defect so the defect section is barely visible in the image.

Figure 6C:
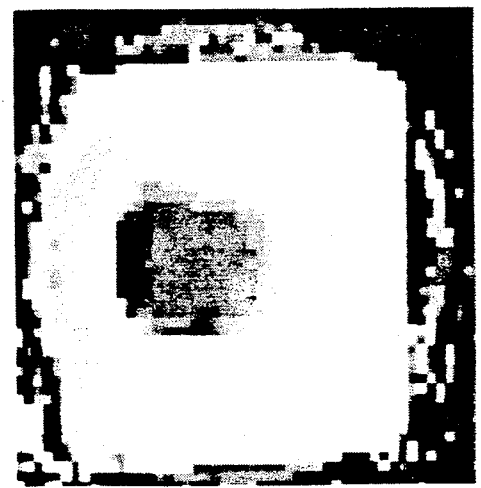
FIG. 6(c) is a photograph of an image obtained when the method of this invention is applied to the same sample.

FIG. 6(c) is a photograph of an image based on the phase difference obtained by processing the above two phase signals. The defect section of the small imbedded copper plate is distinctly visible. The thermal diffusion length of the modulated light of 2 kHz frequency through the sample is approximately 200 μm, while the thermal diffusion length of the 109 Hz light is approximately 600 μm.

As is clear from the above description, according to this invention, when the photoacoustic effect is used to image the interior of an object, in contrast to the conventional method of obtaining an image from only modulated light of a single modulation frequency, in this invention, by using modulated light which is modulated to have two different frequencies, the effect of noise on the images obtained can be reduced and the plane to be observed can be moved from the object surface in the depth direction so that images can be obtained at any desired depth.

What is claimed is:

1. A photoacoustic imaging method in which an object to be observed is illuminated with modulated light and then any sound generated by thermal strain of said object is detected by an acoustic sensor, amplified and converted to an image, said method comprising the steps of:
   illuminating said object with first light modulated to a frequency which generates a first thermal diffusion length of said object;
   detecting a sound generated by the illumination with said first light as a first photoacoustic signal by the use of a photoacoustic sensor;
   illuminating said object with second light modulated to a frequency which generates a second thermal diffusion length of said object;
   detecting a sound generated by the illumination with said second light as a second photoacoustic signal by the use of said photoacoustic sensor;
   determining intensities of said first and second photoacoustic signals thus detected;
   calculating a ratio between said intensities; and imaging a region at a specific depth between said first and second thermal diffusion lengths of said object on the basis of said ratio thus obtained.

2. A photoacoustic imaging method in which an object to be observed is illuminated with modulated light and then any sound generated by thermal strain of said object is detected by an acoustic sensor, amplified and converted to an image, said method comprising the steps of:

illuminating said object with first light modulated to a frequency which generates a first thermal diffusion length of said object;

detecting a sound generated by the illumination with said first light as a first photoacoustic signal by the use of a photoacoustic sensor;

illuminating said object with second light modulated to a frequency which generates a second thermal diffusion length of said object;

detecting a sound generated by the illumination with said second light as a second photoacoustic signal by the use of said photoacoustic sensor;

determining phases of said first and second photoacoustic signals thus detected;

calculating a phase difference between said phases; and imaging a region at a specific depth between said first and second thermal diffusion lengths of said object on the basis of said phase difference obtained.

* * * * *